United States Patent [19]
Johs

[11] Patent Number: 5,929,993
[45] Date of Patent: Jul. 27, 1999

[54] TOTAL FILM RETARDANCE MONITORING SYSTEM, AND METHOD OF USE

[75] Inventor: Blaine D. Johs, Lincoln, Nebr.

[73] Assignee: J.A. Woollam Co. Inc., Lincoln, Nebr.

[21] Appl. No.: 09/033,972

[22] Filed: Mar. 3, 1998

[51] Int. Cl.[6] .................................................. G01N 21/23
[52] U.S. Cl. ..................... 356/364; 356/365; 356/366; 356/367; 356/368
[58] Field of Search .................................. 356/364–368, 356/381, 382, 430, 429

[56] References Cited

U.S. PATENT DOCUMENTS

| | | |
|---|---|---|
| 3,274,882 | 9/1966 | Krieger et al. . |
| 3,807,868 | 4/1974 | Simila ........................................ 356/118 |
| 4,523,848 | 6/1985 | Gorman et al. . |
| 4,584,476 | 4/1986 | Colombotto et al. . |
| 4,909,630 | 3/1990 | Gawrisch et al. . |
| 5,191,392 | 3/1993 | Johnson .................................... 356/353 |

FOREIGN PATENT DOCUMENTS 2338305  2/1975  Germany .

Primary Examiner—Robert H. Kim
Assistant Examiner—Layla Lauchman
Attorney, Agent, or Firm—James D. Welch

[57] ABSTRACT

Disclosed is dual-polarizer based system, and method for continuously monitoring the "total film retardance" of a birefringent film, where "total film retardance" is defined as the product of the difference in the indicies of refraction in the two directions of refringence in said film, multiplied with film thickness. The preferred embodiment involves the application of Fourier analysis to signals which pass through the system and a birefringent film therein, to provide a spectrum, changes in which are indicative of changes in monitored "total film retardance". The present invention allows real time monitoring of birefringent films during manufacture thereof, and, hence, via a control system, control of film manufacturing process parameters to the end that produced films present with a relatively more consistent thickness than is the case where the present invention is not utilized.

13 Claims, 3 Drawing Sheets

TOTAL FILM RETARDANCE MONITORING SYSTEM, AND METHOD OF USE

TECHNICAL FIELD

The present invention relates to the production of articles of manufacture such as photographic films, and more particularly is a system and method for aiding said production by enabling accurate real time monitoring of total birefringent film retardance, and changes therein.

BACKGROUND

A problem in the manufacture of films, such as photographic films, is that accurate real time control over the manufactured thickness thereof is difficult to achieve. In fact, it is estimated that thirty (30%) percent or more of manufactured photographic film is typically out of specification, and must be reprocessed because film manufacturing systems have no reliable, accurate means by which to continuously monitor and control, in real time, manufacturing process results. It should be appreciated that were such a reliable, accurate means by which to continuously monitor film thickness during manufacture thereof available, a feedback control system could be fashioned to effect variation in manufacture process parameters, as required, to keep film thickness within specifications during manufacture and/or handling thereof.

In light of the problem identified infra herein, it is disclosed that the present invention provides a very reliable and accurate Method to continuously monitor the "Total Film Retardance" of a Birefringent Film, (eg. for the purposes of this Disclosure, "Total Film Retardance" is defined as the product of the difference in the Indicies of Refraction ((N1)–(N2)) in the two directions of Refringence in a Film, multiplied with Film Thickness (T), ($\alpha$N·T)). Note that "Total Film Retardance" also implies that a total number of degrees of Retardance is measured, rather than simply some cyclic value between zero (0.0) and three-hundred-sixty (360) degrees. That is, the sum total number of degrees of retardance in numerous sequential cycles can be measured. It should also be appreciated that the present invention does not monitor film thickness per se., but provides indication thereof if changes in Birefringent Refractive Index Optical Properties of a Film are not dominating, with respect to the effects of thickness change in a monitored product of: (the difference between Refractive Indicies in a Birefringent Film multiplied by the thickness of said Birefringent Film). It is to be understood that the presence invention is particularly well suited to reliably and accurately identifying differences in "Total Film Retardance" monitored at different locations on a Birefringent Film, during, for instance, the manufacture thereof.

A search was conducted to identify relevant Patents, and a small number of Patents were identified.

A Patent to Colombotto et al., U.S. Pat. No. 4,584,476 describes a device for non-destructively testing internal stress of heat tempered glass. A system including crossed-polarizers is disclosed, between which crossed polarizers a heat tempered glass sample is positioned in use. The 476 Patent specifies the use of monochromatic infrared radiation.

A Patent to Gorman et al., U.S. Pat. No. 4,523,848 describes a Polarscope which includes first and second quarter wave plates positioned on either side of a birefringent sample under test. In use the quarter wave plates can be switched between two optical conditions to alter the polariscope between a plane polarized and a circularly polarized mode. The 848 Patent describes the use of white light.

A Patent to Simila, U.S. Pat. No. 3,807,868 describes a Method for determining fiber orientation in paper utilizing normally incident light which is reflected therefrom. Polarizers positioned at ninety degrees with respect to one another are present. The polarizers present in the 868 Patent are utilized to isolate quadrature polarized beam components in a polarized beam which reflects from a sample under test. It is also noted that use of monochromatic light is recited in the Claims.

A Patent to Krieger et al., U.S. Pat. No. 3,274,882, similar to the 476 Patent to Colombotto et al., provides apparatus for use in detecting stress in transparent glass sheets. The presence of crossed-polarizers in a light transmission pathway is described as a means to mediate light transmitted through a sheet of glass possessing laminar stress under test and monitored by a detector, as is the presence of a detector to monitor reflected light. Light transmitted through a the crossed-polarizers, and a present or absent sheet of glass therebetween, is utilized in conjunction with reflected light detection means in use.

A Patent to Gawrisch et al, U.S. Pat. No. 4,909,630 describes a system which generates a two dimensional interference image of a biaxially stretched film strip. Areas in said two dimensional interference image which demonstrate different orientation and/or thickness present as "streaks". The use of polychromatic light is described as a means to generating a colored interference image.

Finally, a German Patent, No. DT 23 38 305 A1, describes the presence of crossed-polarizers in a system utilized to detect changes in birefringence of a film placed therebetween.

No known reference, however, teaches that polychromatic light should be transmitted through a system comprised of two polarizers with a birefringent film therebetween, and that a varying intensity pattern, as demonstrated in an Intensity vs. Wavelength plot, should be subjected to mathematical analysis, such as Fourier analysis, to mediate reliable, accurate determination of changes in the "Total Film Retardance" effected by said birefringent film, in response to stresses applied thereto, such as in film manufacturing and/or handling procedures. That is, the present invention allows monitoring Peak Intensity vs. Frequency locations, and changes therein during use, in a mathematically transformed format. Said mathematical transformation serves to improve reliability and accuracy over "crossed-polarizer" system effected monitoring techniques which do not utilize such mathematical transformations, because mathematically transformed results provide more localized and pronounced Peak Intensity vs. Frequency results, to monitor in use.

In view of the identified Patents there remains a need for an improved system and method for use in monitoring total film retardance, particularly in real time during a birefringent film manufacturing process.

DISCLOSURE OF THE INVENTION

Articles of manufacture, such as Films, are prone to present with Varying Thickness and Varying Refringence Properties when subjected to varying fabrication and/or mechanical handling equipment applied forces etc. It is noted that in the manufacture of Photographic Film, for instance, achieving an essentially constant Thickness over an entire length thereof is preferable, if not an absolute requirement regarding producing a technically acceptable product. It is also noted that backing material in Photographic Film presents with "Birefringence" properties.

(Note, Birefringent Films demonstrate certain Refrigent Properties in, for instance, a Direction along the length thereof, and different Refrigent Properties in a direction essentially perpendicular thereto).

The present invention provides a very reliable and accurate Method which allows continuous monitoring of the "Total Film Retardance" of a Birefringent Film. For purposes of this Disclosure, "Total Film Retardance" is defined as the product of the difference in the Indicies of Refraction ((N1)–(N2)) in the two directions of Refringence in said Film, multiplied by Film Thickness (T) at the point at which said Film is investigated (eg. (((N1)–(N2))*(T))). Note that "Total Film Retardance" also implies that a total number of degrees of Retardance is measured, rather than simply some cyclic value between zero (0.0) and three-hundred-sixty (360) degrees. That is the sum total number of degrees of retardance in numerous sequential cycles can be measured.

In general, the present invention provides that when an essentially Linerly Polarized Beam of Light, (effected by passage of a beam of light through a first polarizer), is caused to pass through a Film which demonstrates Birefringence, (ie. a Film which effects different amounts of Retardance between, for instance, Orthogonal Components of a beam of light passing therethrough, depending on how the beam of light is oriented with respect to the two Refringent Directions), and said Polarized Beam direction of essentially Linearly Polarization is oriented other than along one axis of Refringence in said Birefringent Film, then an Varying Intensity Pattern will be created beyond said Birefringent Film (and a second Polarizer), by light exiting said Birefringent Film. Importantly, said Varying Intensity Pattern typically produces a Cyclic Pattern when Intensity vs. a parameter proportional to Wavelength, Frequency or Energy is plotted. The present invention provides that said Cyclic Pattern then be subject to Mathematical Transformation, such as a Fourier analysis, to allow identification of relatively High Intensity Components in a Mathematical transform spectrum representation thereof. As a result, the present invention allows precise monitoring of said relatively High Intensity Mathematical Transform, (eg. Fourier Analysis), provided Components, and/or differences between such Components, and thus provides more precisely identified parameters for use in the detection of changes in Film Thickness and/or Birefringent Properties which give rise to formation of said Varying Intensity Pattern. Differences in relatively High Intensity Component location, and/or separation between relatively High Intensity Components which result where different regions of said Birefringent Film are investigated, are indicative of differences in Film Thickness and/or Birefringent Properties at different locations on said Film. Again, the "Total Film Retardance" as given by:

$$\text{TOTAL FILM RETARDANCE} = (((N1)-(N2))*(\text{THICKNESS})),$$

is provided by use of the present invention.

It is elaborated that the positioning of, and/or spacing between, said relatively High Intensity Components, can be plotted against reciprocal Wavelength, or Frequency, (using Frequency=C/wavelength, where "C" is the speed of light), or Energy, (using Energy=h*Frequency, where h is Plank's constant), or against contrived parameters which are proportional thereto. The "Total Film Retardance" of the Birefringent Film at the point the monitored Beam of Light passes therethrough, and such that changes in said location of, and/or spacing between said relatively High Intensity Frequency Components is indicative of changing Birefringent Film "Total Film Retardance".

A present invention method of continuously monitoring the "Total Film Retardance" of a birefringent film, where Total Film Retardance is defined as:

the product of the difference in the indicies of refraction ((N1)–(N2)) in two directions of refringence in said film, multiplied by film thickness, comprises the steps of:

a. causing at least one beam of light, comprising a multiplicity of wavelengths, to pass through a first polarizer to provide an essentially linearly polarized beam of light;

b. causing said resulting essentially linearly polarized beam of light exiting said first polarizer to pass through a birefringent film, with the direction of said essentially linear polarization of said essentially linearly polarized beam of light oriented other than along a direction of single refringence in said film;

c. causing a resulting beam of light exiting said birefringent film to pass through a second polarizer, such that an varying intensity pattern is formed therebeyond;

d. monitoring a resulting light beam intensity spectrum emerging from said second polarizer, as a function of a parameter proportional to a selection from the group consisting of wavelength, frequency and energy, by use of a detector;

e. performing a mathematical transform of said light beam intensity spectrum verses a parameter proportional to a selection from the group consisting of wavelength, frequency and energy, emerging from said second polarizer, to provide a mathematical transform intensity spectrum verses a parameter proportional to a selection from the group consisting of wavelength, frequency and energy and reciprocals thereof;

said resulting mathematical transform intensity spectrum verses a parameter proportional to a selection from the group consisting of wavelength, frequency and energy and reciprocals thereof, being continuously indicative of the "total film retardance" of said film.

It is noted that the relative magnitudes of a said resulting mathematical transform intensity spectrum peaks is indicative of the "quality" of the data. That is, for instance, if the light beam intensity spectrum emerging from said second polarizer has a strong single frequency component content then the magnitude of a corresponding peak in a mathematically transformed plot will be relatively high. However, if said light beam intensity spectrum emerging from said second polarizer contains a number of frequency components resulting peaks will be more numerous and less distinct, (ie. their magnitudes, relative to the magnitude which corresponds to a mathematically transformed plot of a light beam intensity spectrum emerging from said second polarizer which contains a strong single frequency, will be small). Good "quality" relatively large magnitude mathematically transformed spectra peaks are preferred in the practice of the present invention.

Said method can also comprise the steps of:

f. providing a feedback control system which serves to alter birefringent film manufacturing and/or handling in real time, to the end that the birefringent film "total film retardance" is maintained at a relatively constant value, as said birefringent film is handled in real time; and g. causing said feedback control system to monitor and react to changes in mathematical transform intensity spectrum verses a parameter proportional to a selection from the group consisting of wavelength, frequency and energy and reciprocals thereof, so as to maintain essentially constant birefringent film "total film retardance" in a processed film in real time.

Said method can also comprise the steps of:

h. developing a template in a controlled experimentation with a test birefringent film, said template comprising correlation between changes in mathematical transform spectrum results, corresponding changes in said birefringent test film "total film retardance", and birefringent test film manufacturing and/or handling parameters which cause said changes;

i. monitoring changes in a similarly developed mathematical transform spectrum obtained when a process birefringent film is monitored in real time;

j. comparing the result obtained in step h. with the results obtained in step i., and k. based upon the comparison in step j. effecting change inmanufacturing and/or handling parameters of said process birefringent film to the end that the "total film retardance" of said process birefringent film is maintained essentially constant in real time.

Said method can also comprise the step of:

l. setting the polarization direction of said second polarizer to a desired acute angle, with respect to the polarization direction of said first polarizer, prior to step c. to improve the "quality" of the mathematical transform intensity spectrum peaks.

It is specifically stated that the above recited steps a. through l. need not be practiced in the sequence presented, but that said steps, or modifications thereof, can be practiced in any functional order, with the focus of the invention being that a mathematical transform of an intensity spectrum verses a parameter proportional to a selection from the group consisting of wavelength, frequency and energy be monitored and utilized in determining "Total Film Retardance".

As indicated, the present invention system can further comprise a Feedback Control System comprised of components which perform various method steps recited infra herein, which Feedback Control System serves to alter the Birefringent Film handling system operation in real time, to the end that the Birefringent Film "Total Film Retardance" is maintained at a relatively constant value, as said Birefringent Film is handled.

Also as indicated, a Template can be developed in a controlled experimentation with a Test Birefringent Film, and programmed into a computer or micro-processor system, said Template comprising correlation between changes in Fourier Analysis results and corresponding changes in said Birefringent TEST Film "Total Film Retardance". In use then, changes in spacing of relatively High Intensity Wavelength Specific Components in a Mathematical, (eg. Fourier Analysis), Spectrum developed when a Process Birefringent Film is monitored, can be compared to said Template, and programmed actions comprised of effecting intended Applied Manufacture Effecting Force Control in response thereto, which programmed actions serve to compensate said detected changes in said Mathematical, (eg. Fourier Analysis), Transformation results.

And further as indicated, other than Fourier Analysis of Detector Output Signals, which other Analysis provides a distinct varying transformed Intensity spectrum can be performed and results similar to those described achieved based upon detecting and compensating changes in said distinct varying transformed Intensity spectrum. However, the present invention utilizes some mathematical transformation as an intermediate, result improving, step to determining change in "Total Film Retardance".

The present invention will be better understood by reference to the Detailed Description of this Disclosure, in conjunction with the Drawings.

SUMMARY OF THE INVENTION

It is a purpose of the present invention to provide means by which total film retardance of a birefringent film can be monitored.

It is a another, and primary purpose of the present invention, to teach that an intensity spectrum vs. a parameter, which intensity spectrum is developed by passing a light beam sequentially through a first polarizer, a birefringent sample and a second polarizer, can be more easily analyzed after being subjected to a mathematical transform.

It is a yet another purpose of the present invention, to teach that an intensity spectrum vs. a parameter such as wavelength, frequency or energy etc., which intensity spectrum is developed by passing a light beam sequentially through a first polarizer, a birefringent sample and a second polarizer, can be more easily analyzed after being subjected to a mathematical transform, (eg. Fourier Transform), which provides an intensity spectrum as a function of a parameter which is proportional to a parameter which is a reciprocal of wavelength, frequency or energy etc.

DETAILED DESCRIPTION

Figure 1:
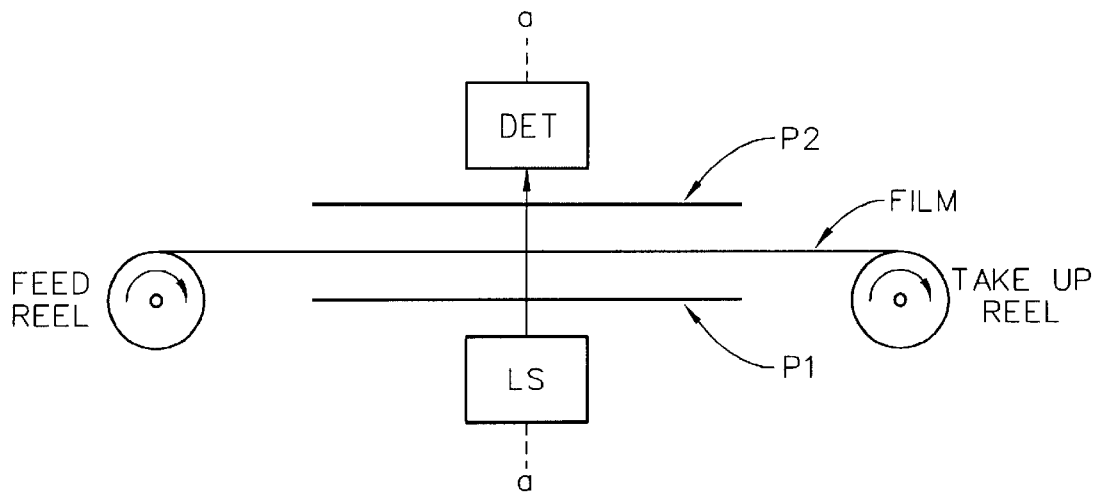
FIG. 1 shows a system demonstrating manufacture and/or handling of films.

Articles of manufacture, such as Films, are prone to present with Varying Thickness and Varying Refringence Properties when subjected to varying forces during manufacture/fabrication and/or mechanical handling etc. As one example, for instance, the accompanying FIG. 1 shows a Film being caused to unwind from a "FEED REEL" and wind onto a "TAKE-UP REEL". If the two "REELS" don't rotate at essentially exactly the same speed at any given time, the Film can become subjected to varying elongation causing forces, and that can cause the Thickness and/or Refringent Properties of the Film, at different locations therealong, to vary. It is noted that in the manufacture of Photographic Film, for instance, an essentially constant Thickness is preferable, if not an absolute requirement. It is also noted that Film utilized as backing material in Photographic Film in particular, presents with "Birefringence". (Note, Birefringent Films demonstrate certain Refringent Properties in, for instance, a Direction along the length thereof, and different Refringent Properties in a direction essentially perpendicular thereto).

Continuing, while aligning an essentially Linearly Polarized Beam of Light, (such as results when light from the Light Source (LS) in FIG. 1 is caused to pass through the First Polarizer (P1)), in a direction along the Length of said Birefringent Film, (assuming said direction in said Birefringent Film is a Direction of Refringence in said Birefringent Film), will then provide some amount of Retardation between Orthogonal Components of said Beam as it exits said Film, and Aligning said essentially Linearly Polarized Beam in a perpendicularly oriented direction will do likewise, (assuming the two directions of Refringence are at ninety (90) degrees to one another), in neither said scenario, can a Variable Intensity Pattern be formed by the Beam(s) exiting said Birefringent Film. However, orienting said First Polarizer (P1) in a direction rotated so as to place said essentially Linearly Polarized Beam Polarization Direction exiting said First Polarizer (P1) which is oriented between said two Directions of Single Refringence in said Birefringent Film, (eg. say at forty-five degrees midway between said Single Refringent Directions, (which are typically oriented at ninety (90) degrees to one another), in said Birefringent Film, (as a nonlimiting example), can lead to formation of a Variable Intensity Pattern vs. Wavelength where the Light exiting said Birefringent Film is also caused to then pass through a second Polarizer (see (P2) in FIG. 1), emphasis added.

Scenarios other than as shown in FIG. 1, in which a Film Thickness and/or Birefringence is caused to vary because of stress applied thereto can also be imagined and all are within the scope of application of the present invention. (Note that a Singly Refringent Film could be monitored by the present invention system, but that only an Optical Path Length measurement could be accomplished. For reasons disclosed herein having to do with creation of a Variable Intensity Pattern of, for instance, Intensity vs. Wavelength, and performance of a Mathematical Transformation (eg. Fourier Analysis), thereupon, the present invention is primarily focused upon investigation of Films which present with Birefringence).

Now, the present invention provides a very accurate Method by which to continuously monitor the "Total Film Retardance" of a Birefringent Film, (eg. for the purposes of this Disclosure, "Total Film Retardance" is defined as the product of the difference in the Indicies of Refraction ((N1)–(N2)) in the two directions of Refringence in said Film, multiplied with Film Thickness (T), (ΔN·T). Note that "Total Film Retardance" also implies that a total number of degrees of Retardance is measured, rather than simply some cyclic value between zero (0.0) and three-hundred-sixty (360) degrees. That is the sum total number of degrees of retardance in numerous sequential cycles can be measured.

Again referring to FIG. 1, it will be further appreciated that the System of the present invention is comprised of two Polarizers (P1) and (P2), which have their Directions of Polarization set at some angle, (eg. typically, but not necessarily, greater than zero (0) and typically, but not necessarily, approximately ninety (90) degrees), with respect to one another, (ie. the Refringent directions are "crossed").

For instance, a Beam of Light exiting a Light Source (LS), (see FIG. 1), and passing through Polarizer (P1), (thereby having imposed a direction of essentially Linear Polarization thereupon), can not reach the Detector (DET) if it is blocked by a Polarizer (P2) with its Polarization Direction rotated a full ninety (90) degrees to with respect to that of Polarizer (P1), unless, for instance a Birefringent Film present between (P1) and (P2) has an effect on the Polarization Direction of the Beam of Light. That is, a beam of Light Polarized by (P1) will be completely blocked by such an oriented Polarizer (P2), unless the Film rotates the Polarizer (P1) imposed Polarization State thereof so that some component of said essentially Linearly Polarized Beam of Light is in the Direction of Polarization of (P2). Now, assuming that the Detector (DET) does monitor some Light, it is to be appreciated that changes in a signal produced by said Detector (DET) will then be caused by changes effected by the Film, as it changes in Thickness and/or it demonstrates changing Birefringence Properties. (Note, the present invention does not require that the Polarizers (P1) and (P2) have their directions of Polarization oriented at ninety (90) degrees, (completely "crossed"), to one another to operate, and the foregoing example was utilized as it is relatively easy scenario to grasp. In fact, in some cases even zero (0) degrees will work).

In general, the present invention provides that an essentially Lineraly Polarized Beam of Light is caused to pass through a Film which demonstrates Birefringence, (ie. a Film which effects different amounts of Retardation between, for instance, Orthogonal Components of a beam of light passing therethrough, depending on how the beam of light is oriented with respect to the two Refringent Directions), and said Polarized Beam direction of essentially Linearly Polarization is oriented other than along one axis of Refringence in said Birefringent Film, then a Variable Intensity Pattern will be created beyond said Birefringent Film, and beyond a second Polarizer (P2), by light exiting said Birefringent Film. Said Variable Intensity Pattern produces a Cyclic Pattern when, for instance, Intensity vs. Wavelength is plotted. Said Cyclic Pattern can be subjected to Mathematical Transformation which allows identification of relatively High Intensity Components in the resulting Mathematically Transformed, (eg. Fourier Analysis), representation thereof. The present invention then allows precise monitoring of said relatively High Intensity Components, and differences therebetween, and thus allows detection of changes in Film Thickness and/or Birefringent Properties which give rise to formation of said Variable Intensity Pattern. Differences in relatively High Intensity Component location, (eg. on a plot vs. Reciprocal Wavelength, Frequency or Energy), and/or separation between relatively High Intensity Components which result where different regions of said Birefringent Film are investigated are indicative of differences in Film Thickness and/or Birefringent Properties at different locations on said Film, (eg. as a Film is passed from Feed to Take-up Reels in FIG. 1). The present invention teaches that application of a Mathematical Transform (eg. Fourier Transform), to Intensity Spectra vs. Wavelength, Frequency or Energy, makes identification of Total Film Retardance much easier. Again, the "Total Film Retardance" as given by:

$$\text{TOTAL FILM RETARDANCE}=(((N1)-(N2))*(\text{THICKNESS})),$$

is investigated by use of the present invention, and where:

$$((N1)-(N2)),$$

is relatively constant, (a reasonable assumption in some cases), changes in Birefringent Sample THICKNESS can be directly monitored.

Figure 2:
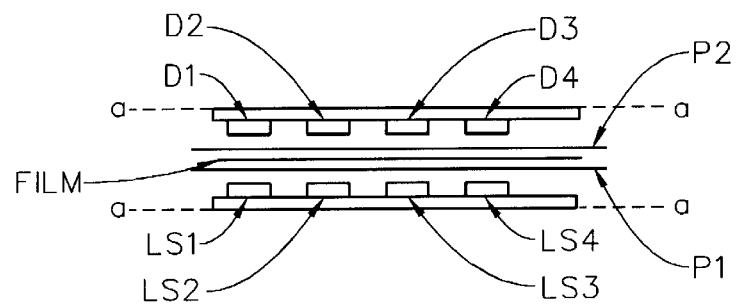
FIG. 2 shows, via a cross section at a—a in FIG. 1, that a system as shown in FIG. 1 can provide the capability to simultaneously monitor multiple points on a film, much as is shown by the system of FIG. 3.
Figure 3:
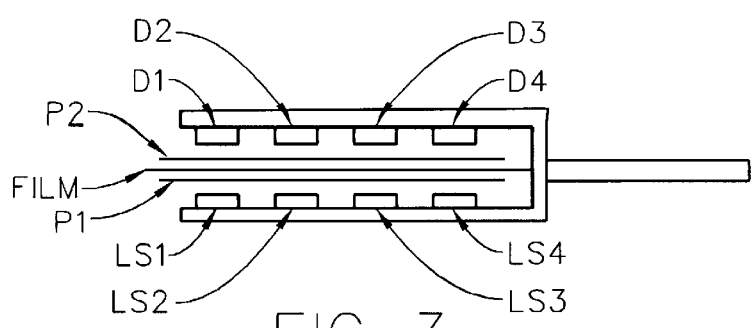
FIG. 3 shows a system for simultaneously monitoring multiple points on a film, comprising multiple light source and detector pairs present in a tuning fork shaped frame.

Continuing, FIG. 2 shows a Cross-Sectional taken at a—a in FIG. 1. It shows that a plurality of Light Beam Sources (LS1), (LS2), (LS3) and (LS4), with accompanying Detectors (D1), (D2), (D3) and (D4). In use each Detector (D1)–(D4) will produce a signal which depends on the Total Film Retardance of the Film at the location at which a Beam of Light from the Corresponding Light Source (LS1)–(LS4)

respectively passes therethrough. FIG. 3 shows that a number of Light Sources (LS1)–(LS4) and Detectors (D1)–(D4) can be mounted to a "Tuning Fork" shaped element and the resulting system can be applied to a Film, to sample "Total Film Retardance" of said Film at various locations thereof. That is, the FIG. 3 system can be moved rather than a Film, as is indicated in FIG. 2.

As indicated by FIGS. 2 and 3, a multiplicity of locations on a Birefringent Film can be simultaneously investigated by a multiplicity of Light Source and Detector Combinations.

A Method of the present invention is was disclosed in the Disclosure of the Invention Section of this Disclosure.

Figure 4:
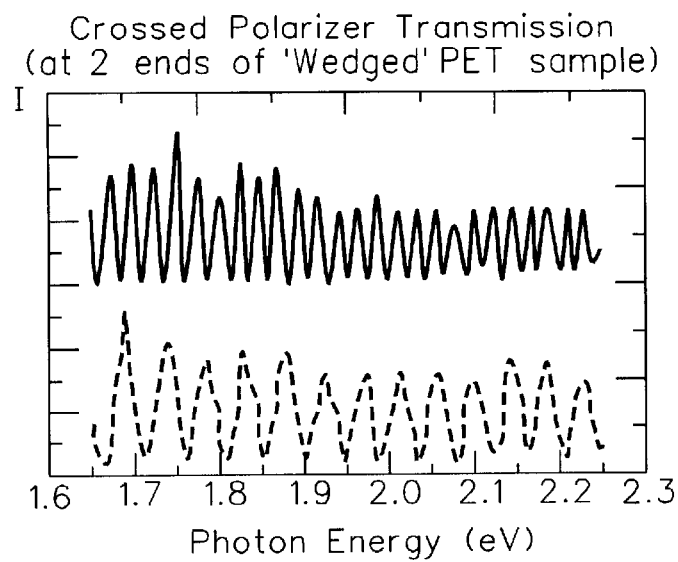
FIG. 4 shows sample dual polarizer birefringent film transmission data spectra.

Turning now to FIG. 4, there are shown two Variable Intensity Pattern Spectra on a single plot. Said two Variable Intensity Pattern Spectra correspond to two sets of transmission data taken at different locations on a wedge-shaped Birefringent Polyethylene Terephthalate (PET which is marketed under the Registered Trademark "MYLAR") sample. That is said two Variable Intensity Pattern Spectra are plots of Intensity verses Energy for two light beams which were caused to pass through a first Polarizer, two different locations on a wedge shaped (PET) sample, and a Second-Polarizer, prior to entering a Detector. Note that the oscillation periodicity is different for different thicknesses of the (PET) sample, and that it is not easy to identify exactly how said two oscillation periods differ by observation of the plots in FIG. 4.

Figure 5:
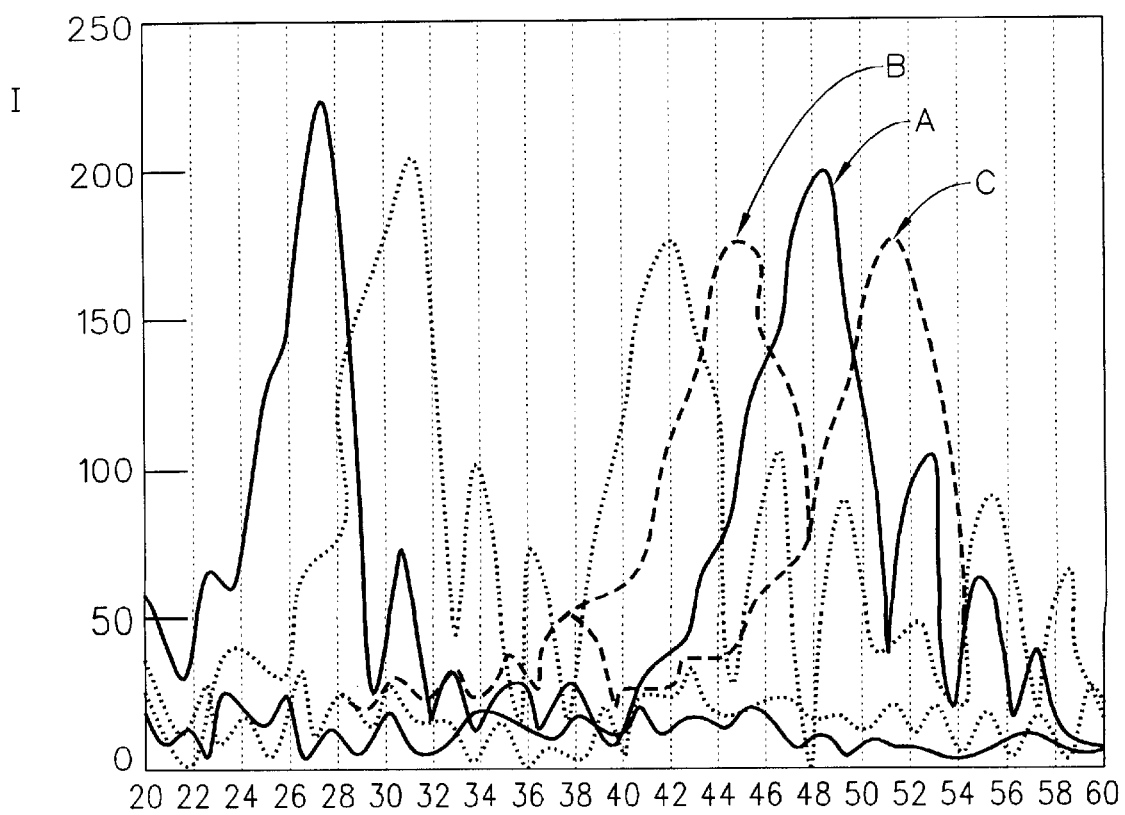
FIG. 5 shows a Fourier transformation of sample dual polarizer birefringent film transmission spectra data such as shown in FIG. 4.

FIG. 5 shows a Fourier Transformed Intensity Spectra, (eg. identified "A", "B" and "C" peaks), for many Variable Intensity Pattern Spectra such as demonstrated in FIG. 4. That is, intensity spectra such as demonstrated in FIG. 4 were obtained for many locations on said wedge shaped (PET) sample, and each was Fourier Transformed to provide results shown in FIG. 5. Note that it is relatively easy to identify differences in the location of high Intensity Components in said Fourier Transformed Spectra, which differences in location correspond to different (ΔN*T) products which correspond to different locations on said (PET) sample. It should be readily appreciated that Mathematically transformed Spectra as shown in FIG. 5 are much easier to analyze than is the Spectra data shown in FIG. 4. FIGS. 4 and 5 then serve to exemplify the present invention utility provided by Mathematically Transforming Spectra data, emphasis added. It is to be understood that adjusting the angle between the first and second Polarizer fast axes can serve to improve the "quality" of the data as shown in FIG. 5, where "quality" indicates the presence of easily identifiable "peaks" with magnitude in excess of background "noise". It is the presence of said easily identifiable peaks shown in FIG. 5 which allows present invention enhanced ability to detect changes in a monitored Birefringent Film. Again, it is much easier to monitor change in magnitude and/or position of identifiable peaks in a Mathematically Transformed Spectrum as shown in FIG. 5, than it is to monitor changes in "waveform" in a FIG. 4 Spectrum.

Figure 6:
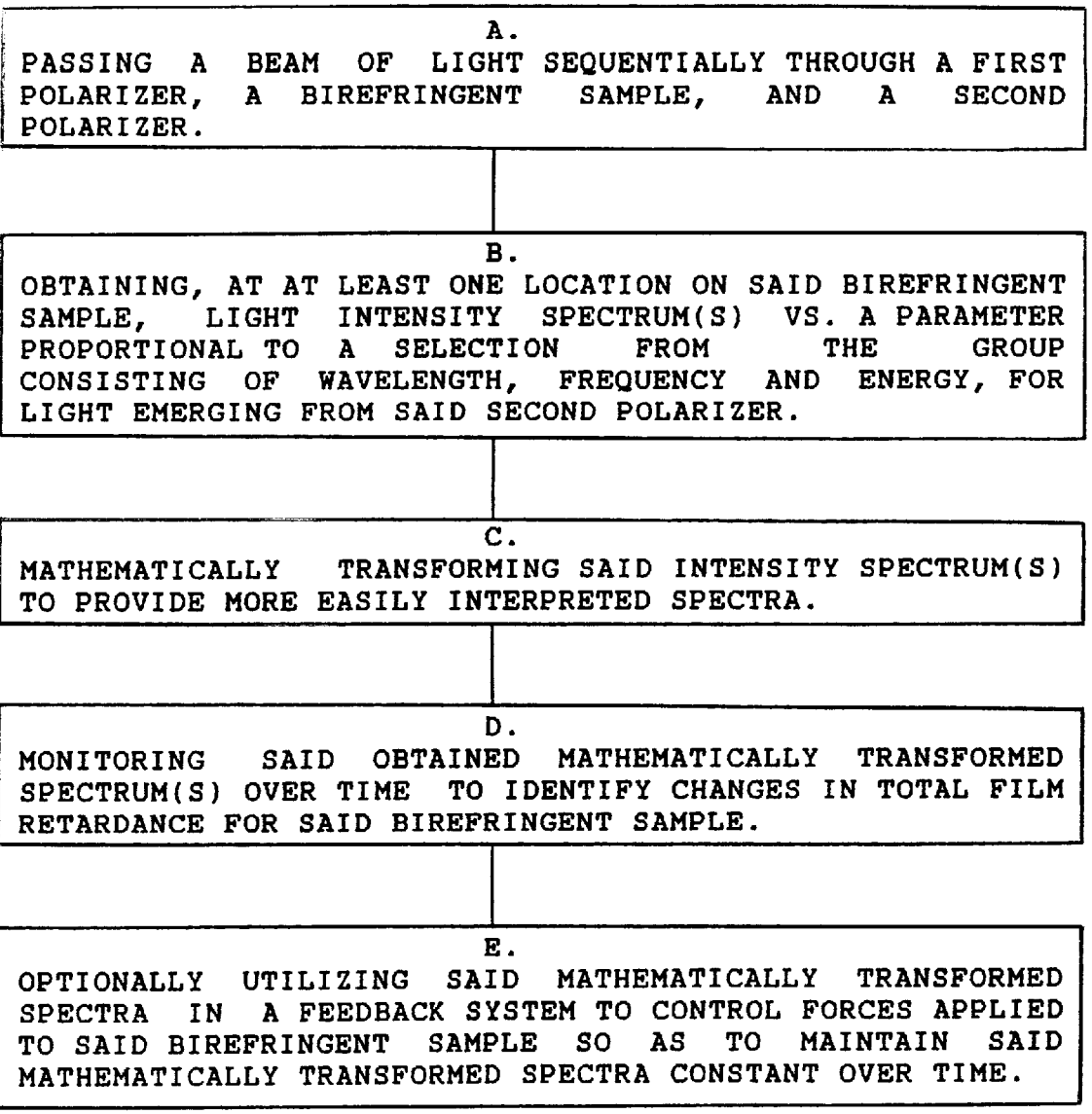
FIG. 6 shows a demonstrative flow diagram of a method of the present invention.

FIG. 6 shows a Flow Chart of Methods of the present invention, said Methods having been described in the Disclosure of the Invention Section of this Disclosure.

The present invention system can further comprise a Feedback Control System which serves to alter the Birefringent Film manufacture and/or handling system operation in real time, to the end that the Birefringent Film "Total Film Retardance" is maintained at a relatively constant value, as said Birefringent Film is manufactured and/or handled, such manufacturing and/or handling being demonstrated by, but not limited to that shown in FIG. 1. This can be accomplished by controlling the Birefringent Film manufacturing and/or handling system operation to the end that identifiable peaks in Mathematically Transformed Intensity Spectra are maintained essentially constant, as regards magnitude and/or position in the Mathematically Transformed Spectra, over time. A particulary relevant approch to use of a involves monitoring position of identifiable relatively high magnitude peaks in a Mathematically Transformed Spectrum such as shown in FIG. 5, and causing said Feedback Control System react so as to keep said identifiable relatively high magnitude peaks in said Mathematically Transformed Spectrum constant in position over time during which a Birefringent Film is processed. Also, a Template can be developed in a controlled experimentation with a TEST Birefringent Film, and programmed into a computer or micro processor system. Said Template comprising correlation between changes in, for instance, Fourier Analysis Spectrum results and corresponding changes in said Birefringent TEST Film "Total Film Retardance". In use then, changes in spacing and/or magnitude of relatively High Intensity Frequency Components in a Fourier Analysis Spectrum developed when a PROCESS Birefringent Film is monitored can be compared to said Template, and programmed actions comprised of effecting intended Applied Force Control in response thereto, which programmed actions serve to compensate said detected changes in said Fourier Analysis results.

It is noted that typical Intensity Spectrums as described herein are plotted with respect to Wavelength, Frequency or Energy and/or reciprocals thereof. However, it is to be understood that other parameters might be used. For the purposes of Claims construction the terminology "proportional to a selection from the group consisting of wavelength, frequency and energy and reciprocals thereof" is to be interpreted to include functional equivalents to wavelength, frequency and energy and/or reciprocals thereof. It is also noted that the term "Intensity" has been applied to describe peaks in a Mathematically Transformed Spectrum as shown in FIG. 5. This usage is to be understood to primarily mean peak height or magnitude, but can be interpreted to relate to peak width or area under the peak etc. as well. That is, it is not specifics of peaks in a FIG. 5 Mathematical Transformed Spectrum which is of primary importance in the present invention, but rather the fact that said peaks are derived and utilized, in constrast to the use of an Intensity Spectrum such as shown in FIG. 4 in the monitoring, (and control), of Birefringent Film manufacture and/or handling processes.

Finally, it is to be understood that the term "light" was used in this Disclosure. Said term is to be interpreted sufficiently broadly to include electromagnetic radiation of any frequency which can be functionally utilized in practice of the present invention.

Having hereby disclosed the subject matter of the present invention, it should be obvious that many modifications, substitutions and variations of the present invention are possible in light of the teachings. It is therefore to be understood that the invention can be practiced other than as specifically described, and should be limited in breadth and scope only by the Claims.

I claim:

1. A method of continuously monitoring the "total film retardance" of a birefringent film, where "total film retardance" of a birefringent film is defined as:

the product of the difference in the indicies of refraction in two directions of refringence in said film, multiplied by film thickness;

said method comprising the steps of:

a. causing at least one beam of light, comprising a multiplicity of wavelengths, to pass through a first polarizer to provide an essentially linearly polarized beam of light;

b. causing said resulting essentially linearly polarized beam of light exiting said first polarizer to pass through a birefringent film, with the direction of said essentially linear polarization of said essentially linearly polarized beam of light oriented other than along a direction of single refringence in said film;

c. causing a resulting beam of light exiting said birefringent film to pass through a second polarizer, such that an varying intensity pattern is formed therebeyond;

d. monitoring a resulting light beam intensity spectrum emerging from said second polarizer, as a function of a parameter proportional to a selection from the group consisting of wavelength, frequency and energy, by use of a detector; and e. performing a mathematical transform of said light beam intensity spectrum verses a parameter proportional to a selection from the group consisting of wavelength, frequency and energy, emerging from said second polarizer, to provide a mathematical transform intensity spectrum verses a parameter proportional to a selection from the group consisting of wavelength, frequency and energy and reciprocals thereof;

said resulting mathematical transform intensity spectrum verses a parameter proportional to a selection from the group consisting of wavelength, frequency and energy and reciprocals, thereof, being continuously indicative of the "total film retardance" of said film.

2. A method of continuously monitoring the "total film retardance" as in claim 1, which further comprises:

a. providing a feedback control system which serves to alter birefringent film handling in real time, to the end that the birefringent film "total film retardance" is maintained at a relatively constant value, as said birefringent film is manufactured and/or handled in real tine; and b. causing said feedback control system to monitor and react to changes in mathematical transform intensity spectrum verses a parameter proportional to a selection from the group consisting of wavelength, frequency and energy and reciprocals thereof, to maintain essentially constant birefringent film "total film retardance" in a processed film in real time.

3. A method of continuously monitoring the "total film retardance" as in claim 1, which further comprises:

a. developing a template in a controlled experimentation with a test birefringent film, said template comprising correlation between changes in mathematical transform spectrum results corresponding to changes in said birefringent test film "total film retardance", and birefringent test film manufacturing and/or handling parameters which cause said changes;

b. monitoring changes in a similarly developed mathematical transform spectrum obtained when a process birefringent film is monitored in real time;

c. comparing the result obtained in step b. with the results obtained in step a., and d. based upon the comparison in step c. effecting change in manufacturing and/or handling parameters of said process birefringent film to the end that the "total film retardance" of said process birefringent film is maintained essentially constant in real time.

4. A method of continuously monitoring the "total film retardance" as in claim 1, which further comprises the step of setting the polarization direction of said second polarizer to a desired acute angle, with respect to the polarization direction of said first polarizer, prior to step d.

5. A method of continuously monitoring the "total film retardance" as in claim 2, in which the step of performing a mathematical transform to said intensity spectrum verses a parameter proportional to a selection from the group consisting of wavelength, frequency and energy provides a spectrum which has identifiable peaks therein as plotted against a parameter proportional to a selection from the group consisting of wavelength, frequency and energy and reciprocals thereof, the magnitude and/or position of said identifiable peaks monitored serving to provide indication of "total film retardance" of said monitored birefringent film.

6. A method of continuously monitoring the "total film retardance" as in claim 1, in which the step of performing a mathematical transform involves performing a Fourier analysis.

7. A method of continuously monitoring the "total film retardance" as in claim 2, in which the step of performing a mathematical transform Involves performing a Fourier analysis.

8. A method of continuously monitoring the "total film retardance" as In claim 3, in which the step of performing a mathematical transform involves performing a Fourier analysis.

9. A method of continuously monitoring the "total film retardance" as in claim 4, in which the step of performing a mathematical transform involves performing a Fourier analysis.

10. A method of continuously monitoring the "total film retardance" as in claim 5, in which the step of performing a mathematical transform involves performing a Fourier analysis.

11. A system comprising means for:

a. causing at least one beam of light, comprising a multiplicity of wavelengths, to pass through a first polarizer to provide an essentially linearly polarized beam of light;

b. causing said resulting essentially linearly polarized beam of light exiting said first polarizer to pass through a birefringent film, with the direction of said essentially linear polarization of said essentially linearly polarized beam of light oriented other than along a direction of single refringence in said film;

c. causing a resulting beam of light exiting said birefringent film to pass through a second polarizer, such that an varying intensity pattern is formed therebeyond;

d. monitoring a resulting light beam intensity spectrum emerging from said second polarizer, as a function of a parameter proportional to a selection from the group consisting of wavelength, frequency and energy, by use of a detector;

e. performing a mathematical transform of said light beam intensity spectrum verses a parameter proportional to a selection from the group consisting of wavelength, frequency and energy, emerging from said second polarizer, to provide a mathematical transform intensity spectrum verses a parameter proportional to a selection from the group consisting of wavelength, frequency and energy and reciprocals thereof;

said resulting mathematical transform intensity spectrum verses a parameter proportional to a selection from the group consisting of wavelength, frequency and energy, and reciprocals thereof being continuously indicative of the "total film retardance" of said film.

12. A system as in claim 11, which further comprises:

a. a feedback control system means which serves to alter birefringent film handling in real time, to the end that the birefringent film "total film retardance" is maintained at a relatively constant value, as said birefringent film is manufactured and/or handled in real time; and b. said feedback control system comprising means to monitor and react to changes in mathematical transform intensity spectrum verses a parameter proportional to a selection from the group consisting of wavelength, frequency and energy, and reciprocals thereof, to maintain essentially constant birefringent film "total film retardance" in a processed film in real time.

13. A system as in claim 11, which further comprises means for:

a. developing a template in a controlled experimentation with a test birefringent film, said template comprising correlation between changes in mathematical transform spectrum results, corresponding changes in said birefringent test film "total film retardance", and birefringent test film manufacturing and/or handling parameters which cause said changes;

b. monitoring changes in a similarly developed mathematical transform spectrum obtained when a process birefringent film is monitored in real time;

c. comparing the result obtained in step b. with the results obtained in step a., and d. based upon the comparison in step c. effecting change in handling parameters of said process birefringent film to the end that the "total film retardance" of said process birefringent film is maintained essentially constant in real time.

* * * * *